United States Patent [19]

Yokelson et al.

[11] Patent Number: 4,940,810
[45] Date of Patent: Jul. 10, 1990

[54] PROCESS FOR PRODUCING SILICON-CONTAINING AROMATIC POLYACIDS

[75] Inventors: Howard B. Yokelson, Aurora; Walter Partenheimer, Naperville; Robert Gipe, Wheaton, all of Ill.

[73] Assignee: Amoco Corporation, Chicago, Ill.

[21] Appl. No.: 451,412

[22] Filed: Dec. 15, 1989

[51] Int. Cl.$^5$ .............................. C07F 7/08; C07F 7/18
[52] U.S. Cl. ....................................................... 556/438
[58] Field of Search .......................................... 556/438

[56] References Cited

U.S. PATENT DOCUMENTS 4,176,124 11/1979 Darms et al. ................... 556/438 X Primary Examiner—Paul F. Shaver
Attorney, Agent, or Firm—Gunar J. Blumberg; William H. Magidson; Ralph C. Medhurst

[57] ABSTRACT

An improved process is disclosed for preparation of silicon-containing aromatic polyacids by liquid phase oxidation of a mono- or polyalkyl substituted diaryl-dialkylsilane in the presence of oxygen and a catalyst comprising cobalt-manganese-bromine. Bis(p-tolyl)-dimethylsilane is oxidized to bis(p-carboxyphenyl)dimethylsilane and bis(3,4-dimethylphenyl)-dimethylsilane is oxidized to bis(3,4-dicarboxylphenyl)dimethylsilane.

6 Claims, No Drawings

PROCESS FOR PRODUCING SILICON-CONTAINING AROMATIC POLYACIDS

FIELD OF THE INVENTION

The field of the invention relates to a process for preparation of silicon-containing aromatic polyacids by a liquid-phase oxidation of a mono- or poly-alkyl-substituted diaryl compound comprising an alkyl-substituted diaryl dialkyl silane wherein alkyl groups in the alkyl-substituted diaryl group contain from 1 to 20 carbon atoms, the number of alkyl groups on the alkyl-substituted diaryl groups are from 1 to 4, and the alkyl groups on the silicon atom contain from 1 to 20 carbon atoms to prepare bis(carboxyphenyl)dialkyl-substituted silane compounds. More particularly, the field of the invention relates to the preparation of bis(p-carboxyphenyl)dimethylsilane and bis(3,4-dicarboxyphenyl)-dimethylsilane by oxidation of bis(p-tolyl)dimethylsilane and bis(3,4-dimethylphenyl)dimethylsilane, respectively, in the presence of a cobalt-manganese-bromine catalyst.

BACKGROUND OF THE INVENTION

Organosilicon polymers, as a class of engineering thermoplastics, have good heat resistance and excellent mechanical properties in the form of polyesters and polyamides. A precursor for polyesters and polyamides having organosilicon segments is necessarily a polyfunctional molecule containing an organosilicon moiety, preferably of a polycarboxylic character which can be reacted readily with an alcohol or an amine, etc., to produce a polyester or polyamide, etc. of suitable chain length. Such precursors include silicon-containing aromatic polyacids such as bis(p-carboxylphenyl)dimethylsilane.

Previous investigators have prepared bis(carboxyphenyl) silanes by oxidation of the corresponding bis-(alkyaryl)tetravalent silicon compounds. Examples in the literature claim successful conversions with a variety of oxidation reagents and conditions.

Tyler, U.S. Pat. No. 2,517,146 teaches the oxidation of ditolydimethylsilane by heating the silane with alkaline potassium permanganate or by passing the silane at elevated temperatures in air over a metallic oxide catalyst such as manganese dioxide or chromium trioxide. A second method taught by Tyler is by carbonating the Grignard reagent of dibromophenyldimethylsilane. The Grignard reagent of the silane is reacted with an excess of solid carbon dioxide powder. The resulting dicarboxyphenyldimethylsilane was reacted with polyhydric alcohols and polyfunctional amines to produce resins of the polyamide and alkyd types.

Speck, U.S. Pat. No. 2,722,524, teaches hydrolysis of bis(p-cyanophenyl) dimethylsilane with potassium hydroxide in ethyl alcohol and water to prepare the diacid. Speck also teaches the oxidation of ditolydiphenylsilane with potassium permanganate in a hot aqueous pyridine system. The hexamethylenediamine salt of the bis(p-carboxyphenyl) dimethylsilane was polymerized by the salt fusion technique. The resulting polymer was a tough, clear colorless film. Polyester fibers prepared from the diacid with ethylene glycol had good initial tensile modulus, elastic recovery, orientation along the fiber axis, as well as good strength and dyeing characteristics.

Japanese Patent Publication No. 310846/1988 teaches a batch process for production of a diaryl dicarboxylic acid containing a substituted carbon or substituted silicon atom by oxidizing a corresponding dialkyl-substituted diaryl compound with molecular oxygen in the presence of a catalyst comprising cobalt, bromine and chlorine, and a heavy metal preferably selected from the group consisting of manganese, cerium, zirconium, chromium and nickel. A 95% yield was reported of bis(4-carboxyphenyl)dimethylsilane in the presence of a cobalt, manganese, bromine, and chlorine catalyst wherein the mole ratios of the catalyst components were 48:4:46:48 millimoles, respectively.

Despite the above-reported methods of preparing bis(4-carboxylphenyl) dimethylsilane, each process has disadvantages in the manufacture of the diacid at a low cost on an industrial scale. The permanganate method results in the production of undesirable by-products, including manganese dioxide. The reaction of the Grignard reagent with solid carbon dioxide requires the use of the Grignard reaction to prepare the precursor. It also results in a large amount of undesirable products. The oxidation of a bis(alkylphenyl) dialkylsilane in the presence of a catalyst comprising chlorine in the form of concentrated hydrochloric acid requires special corrosion-resistant process equipment.

Accordingly, it is an object of this invention to provide an improved method which overcomes the aforesaid problems of prior art methods by the liquid phase oxidation of an alkyl-substituted diaryl dialkyl silane with an oxygen-containing gas in a solvent and in the presence of an oxidation catalyst.

More particularly, it is an object of this invention to provide an improved method for preparing bis(p-carboxyphenyl) dimethylsilane and bis(3,4-dicarboxyphenyl)dimethylsilane in the presence of a cobalt-manganese-bromine catalyst wherein problems of corrosion of process equipment are overcome in a low-cost, economical, industrially advantageous process which is suitable for large scale production of silicon-containing aromatic polyacids.

SUMMARY OF THE INVENTION

A process is disclosed for the production of bis(-mono- or polycarboxyaryl) alkylsilane compounds in a liquid phase oxidation of a mono- or polyalkylphenyl-dialkyesilane with an oxygen-containing gas in a solvent at an elevated temperature and pressure and in the presence of an oxidation catalyst comprising cobalt, manganese, and bromine components.

DETAILS OF THE INVENTION

The instant invented process for the oxidation of bis(p-tolyl) dimethylsilane and bis(3,4-dimethylphenyl)-dimethylsilane is applicable to oxidation of any alkyl-substituted diaryl dialkyl silane wherein alkyl groups in the alkyl-substituted diaryl group contain from 1 to 20 carbon atoms, the number of alkyl groups on the alkyl-substituted diaryl groups are from 1 to 4, and the alkyl groups on the silyl group contain from 1 to 20 carbon atoms. In preferred embodiments of the method of this invention, bis(p-methylphenyl) dimethylsilane is oxidized to bis(p-carboxyphenyl) dimethylsilane and bis(3,4-dimethylphenyl)dimethylsilane is oxidized to bis(3,4-dicarboxyphenyl)dimethylsilane. The invented process can be in batch, semi-continuous or continuous method.

Suitable solvents for use in the instant invented process include any aliphatic $C_2$–$C_6$ monocarboxylic acid such as acetic acid, propionic acid, n-butyric acid, isobutyric acid, n-valeric acid, trimethylacetic and caproic acid and mixtures thereof. Preferably, the solvent is glacial acetic acid. The solvent can comprise a mixture of glacial acetic acid and acetic anhydride. Hydrolysis of the Si-C bond can occur in the presence of water. In the oxidation reactor slurry, the solvent preferably comprises less than 0.5 wt. percent of water.

Since water is produced by the oxidation reaction, rate of production of water at a steady rate is controlled by the feed stream water concentration and the rates of withdraw of condensate and vapor from reactors and crystallizers, where the withdrawn material is dehydrated and then recycled. Low water concentration in the reaction increases production of the diacid. Reaction water concentration below 1 wt. % is preferable, more preferably below 0.5 wt. %.

When reactor slurry by-product concentration has exceeded a critical concentration because of changes in process parameters, by-product concentration can be adjusted by adjusting the reactor oxygen partial pressure. Rate of feed and pressure of an oxygen-containing gas controls oxygen partial pressure in the reaction mixture.

The source of molecular oxygen employed in a continuous method of this invention can vary in molecular oxygen content from that of air to oxygen gas. Air is the preferred source of molecular oxygen. In order to avoid the formation of explosive mixtures in a continuous method, the oxygen-containing gas fed to the reactor should provide an exhaust gas-vapor mixture containing from 0.5 to 8 volume percent oxygen (measured on a solvent-free basis). For example, when each alkyl substitutent on the aromatic ring of the alkyl aryl silane is a methyl group, a feed rate of the amount of from 1.5 to 2.8 moles per methyl group will provide such 0.5 to 8 volume percent of oxygen (measured on a solvent-free basis) in the gas-vapor mixture in the condenser. Accordingly, reactor vent oxygen as volume percent of dry off gas can be in the range of from about 1 to about 6, preferably about 4.0 vol. % of vent gas on a dry basis.

The catalyst employed in the method of this invention comprises cobalt, manganese and bromine components, and can additionally comprise accelerators known in the art. The weight ratio of cobalt (calculated as elemental cobalt) in the cobalt component of the catalyst to the alkyl-substituted diaryl dialkyl silane in the liquid phase oxidation of the method of this invention is in the range of from about 0.2 to about 100 milligram atoms (mga) per gram mole of the alkyl-substituted diaryl dialkyl silane. The weight ratio of manganese (calculated as elemental manganese) in the manganese component of the catalyst to cobalt (calculated as elemental cobalt) in the cobalt component of the catalyst in the liquid phase oxidation of the method of this invention is in the range of from about 0.2 to about 10 mga per mga of cobalt. The weight ratio of bromine (calculated as elemental bromine) in the bromine component of the catalyst to total cobalt and manganese (calculated as elemental cobalt and elemental manganese) in the cobalt and manganese components of the catalyst in the liquid phase oxidation of the method of this invention is in range of from about 0.25 to about 1.2 mga per mga of total cobalt and manganese.

When reactor slurry by-product concentration has exceeded its critical concentration because of changes in process parameters, by-product concentration can be adjusted by adjusting the reactor solvent mole ratio of bromine to cobalt plus manganese.

Each of the cobalt, manganese and bromine components can be provided in any of the known ionic or combined forms that provide soluble forms of cobalt, manganese and bromine in the solvent in the reactor. For example, when the solvent is an acetic acid medium, cobalt and/or manganese, acetate tetrahydrate, and hydrogen bromide can be employed. The 0.25 to 1.2 bromine-to-total cobalt and manganese milligram atom ratio is provided by a suitable source of bromine. Bromine sources include elemental bromine ($Br_2$), ionic bromide (for example, NaBr, KBr, $NH_4Br$, etc.), or organic bromides which are known to provide bromide ions at the operating temperature of the oxidation (e.g., bromobenzenes, benzylbromide, mono-and dibromoacetic acid, bromoacetyl bromide, tetrabromoethane, ethylenedibromide, etc.). The total bromine in molecular bromine and ionic bromide is used to satisfy the bromine to metal atom ratio of 0.25 to 1.2. The bromide ion released from the organic bromides at the oxidation operating conditions can be readily determined by known analytical means. Tetrabromoethane, for example, at operating temperatures of about 340° F. (170° C.) to about 440° F. (225° C.) has been found to yield about 3 effective gram atoms of bromine per gram mole.

NaBr is preferred as a source of bromine. Hydrolysis of the Si—C bond can occur in the presence of water produced by the reaction or as a component of a reactant if such is used, such as hydrobromic acid.

The invented process can be in batch, semi-continuous or continuous method. A continuous method is preferred. Since the reaction produces water as a by-product, the increasing concentration of water with time that occurs in a batch reaction can cause the hydrolysis of the Si—C bond with increased formation of by-products such as benzoic acid or hexamethylcyclotrisiloxane, with corresponding loss of product yield.

In the continuous method of operation, the oxidation feed comprising an alkyl-substituted diaryl diakyl silane, a source of oxygen, preferably air, a solvent, preferably glacial acetic acid or a mixture of glacial acetic acid and acetic anhydride, and catalyst are fed to the reaction zone at a rate such that preferred per pass oxidations are attained to prepare the desired carboxyphenyl dialkyl silane. Depending upon equipment limitations, volumetric space velocity of the feed will determine contact time in the reaction zone and rate of production of water by the reaction.

Concentration of the alkyl-substituted diaryldialkylsilane relative to the solvent has been found to preferably in the range of from about 1:10 to about 1:5, ratio of the alkyl-substituted diaaryldialkylsilane to the solvent based upon weight.

From the exit end of the reaction zone in a continuous process, there is withdrawn an effluent comprising the oxidized product, by-product oxygenated silane compounds, inert gas or gases, unreacted feed components, oxygen and water vapor. The effluent is passed to a separation zone in which the reaction products are separated and desired product substantially recovered. The remaining effluent after removal of the water can be returned to the reaction zone.

In an embodiment of the process of this invention, di(p-tolyl)dimethylsilane is oxidized to bis(p-carboxyphenyl)dimethylsilane in the presence of a cobalt-manganese bromine catalyst in a solute comprising glacial acetic acid at a temperature within the range of from about 120° C. (250° F.) to about 260° C. (500° F.). Below 100° C., virtually no reaction occurs. Above about 260° C., the bis(p-carboxyphenyl)dimethylsilane is unstable with consequent decomposition and loss of product. Preferably, reaction temperature is in the range of from about 145° C. (293° F.) to about 165° C. (329° F.). Reaction pressure is in the range of from about 50 psig to about 750 psig, preferably from about 300 psig to about 600 psig. At pressures below 50 psig, virtually no reaction occurs. Pressures above 750 psig require high pressure process equipment with attendant economic costs.

In operation, the minimum pressure at which the reactor is maintained is that pressure which will maintain a substantial liquid phase of the alkyarylsilane and at least 70 percent of the solvent. The alkylarylsilane and solvent not in the liquid phase because of vaporization can be removed from the reactor as vapor-gas mixture, condensed and returned to the reactor. When the solvent is an acetic acid mixture, suitable reaction gauge pressure is in the range of from about 150 psig to about 600 psig, and typically is in the range of from about 250 psig to about 550 psig. The temperature range within the reactor is generally from about 120° C. (250° F.) to about 260° C. (500° F.), preferably from about 150° C. (300° F.), to about 165° C. (329° F.).

The instant invention comprises a batch, semi-continuous or continuous liquid phase process in a suitable reactor for the production of a bis(polycarboxyaryl)-dialkylsilane, wherein the feedstream contains a dialkylphenyldialkylsilane, by oxidation of a said dialkylphenyldialkylsilane in the presence of a cobalt-manganese-bromine catalyst which process comprises: (a) preparing a reaction mixture containing an aliphatic $C_2$-$C_6$ monocarboxylic acid and said silane, wherein water concentration is less than about 1.0 wt. %, preferably less than about 0.5 wt. %, wherein mole ratio of bromine to cobalt plus manganese of said catalyst is in the range of from about 0.35 to about 0.75; (b) treating the reaction mixture with an oxygen-containing gas wherein vent oxygen in volume percent is from 0.5 to 8 volume % (measured on a solvent-free basis) to cause oxidation of the said dialkylphenyldialkylsilane to a bis(polycarboxyaryl)dimethylsilane as product at a reaction temperature and at a reaction pressure to maintain the aqueous mixture in liquid phase; c) recovering said bis(polycarboxyaryl) dialkylsilane as product from said reaction mixture wherein presence of reactor slurry by-product concentration is less than or no greater than a critical concentration determined principally by the reactor solvent mole ratio of bromine to cobalt plus manganese concentration at a temperature within the range of from about 140° C. (284° F.) to about 165° C. (329° F.).

In summary, the instant invention comprises a process for preparation of silicon-containing aromatic polyacids by liquid phase oxidation of an alkyl-substituted diaryldialkylsilane wherein alkyl groups containing 1 to 20 carbon atoms in the alkyl-substituted diaryl group number from 1 to 4, and the number of carbon atoms is from 1 to 20 in the alkyl groups attached to the silicon of the silane group, which process comprises; (a) introducing into a suitable reactor a feedstock comprising said alkyl-substituted diaryldialkylsilane in a solvent comprising an aliphatic $C_2$ to $C_6$ monocarboxylic acid; (b) oxidizing said feedstock in the presence of a catalyst comprising cobalt-manganese-bromine with an oxygen-containing gas wherein the weight ratio of cobalt (calculated as elemental cobalt) to the alkyl-substituted diaryldialkylsilane is in the range of from about 0.2 to about 100 milligram atoms (mga) per gram mole of said alkyl-substituted diaryldialkylsilane, weight ratio of manganese (calculated as elemental manganese) to the cobalt of said catalyst is in the range of from about 0.2 to 100 milligram atoms (mga) per mga of cobalt, and weight ratio of bromine in said catalyst (calculated as elemental bromine) to cobalt and manganese (calculated as elemental cobalt and manganese) is in the range of from about 0.25 to about 1.2 mga per mga of total cobalt and manganese, wherein said feedstock is present in a weight ratio to said aliphatic $C_2$ to $C_6$ monocarboxylic acid wherein the ratio of said feedstock to said acid is in the range of from about 1:10 to about 1:5 at a temperature within the range of from about 120° C. (250° F.). to about 260° C. (500° F.) and at a reaction pressure within the range of from about 50 psig to about 750 psig; and (c) recovering a silicon-containing aromatic polyacid wherein said polyacid comprises bis(mono- or polycarboxyaryl)dialkylsilane.

In more detail, the instant invention comprises a process wherein said feedstock comprising an alkyl-substituted diaryl dialkylsilane is selected from the group consisting of bis(p-tolyl) dimethylsilane and bis(3,4-dimethylphenyl)dimethylsilane. The said feedstock can comprise bis(p-tolyl) dimethylsilane, said $C_2$ to $C_6$ monocarboxylic acid is acetic acid, and said silicon-containing aromatic polyacid comprises bis(p-carboxyphenyl) dimethylsilane.

The said feedstock can comprise bis(3,4-dimethylphenyl)dimethylsilane, said $C_2$ to $C_6$ monocarboxylic acid is acetic acid, and said silicon-containing aromatic polyacid comprises bis(3,4-dicarboxyphenyl) dimethylsilane.

In one embodiment, the said oxygen-containing gas is air and said process is a continuous process wherein said oxygen-containing gas fed to said reactor provides an exhaust gas-vapor mixture containing from 0.5 to 8 volume percent oxygen, measured on a solvent-free basis.

In further detail, in an embodiment of the continuous method of the instant invention, the feedstock is selected from the group consisting of bis(p-tolyl)dimethylsilane and bis(3,4-dimethylphenyl) dimethylsilane, the $C_2$ to $C_6$ monocarboxylic acid is acetic acid, the mole ratio of manganese to cobalt is in the range of from about 0.2 to about 10.0, mole ratio of bromine to total cobalt plus manganese is about 0.2 to about 1.2, weight ratio of cobalt to said acetic acid, as glacial acetic acid, is in the range of from about 250 ppm to about 750 ppm, water content of the reaction mixture is from about 0.5 wt. % to about 2.0 wt. % reaction temperature is in the range of from about 140° C. to about 165° C., reaction pressure is within the range of from about 200 psig to about 550 psig, and residence time is from about 30 minutes to about 6 hours.

The following examples illustrate the process of the invention but are not to be considered as limiting the scope of the invention.

EXAMPLE I

The following example illustrates that low reaction temperature and pressure are unsuitable for oxidation of bis(p-tolyl) dimethylsilane to bis(p-carboxyphenyl) dimethylsilane in presence of a cobalt-manganese-bromine catalyst.

The initial reaction was in a glass reactor at 100° C. and ambient atmospheric pressure using a Co/Mn/Br catalyst. A solution of 0.500 g of Co(II) acetate tetrahydrate, 0.492 g of Mn(II) acetate tetrahydrate, 0.413 g of sodium bromide in 100 ml acetic acid was heated to 94° C. Air was passed through the solution via a glass frit at 50 ml/min. and 19.74 g of bis(p-tolyl) dimethylsilane was added in one portion. There was no sign of oxygen uptake as indicated by the vent dioxygen value of 20.9% (measured on a Beckman oxygen meter). Addition of 0.050 g of zirconium oxide acetate, and subsequently another increment of Co/Mn/Br to the reaction mixture did not result in any oxygen uptake.

Because of the very slow rate of oxygen uptake (if any) indicated above, acetic acid and more catalyst were added, and the resultant solution was placed in an autoclave to subject the mixture to higher temperatures and pressures. An additional 300 ml of acetic acid was added, as well as 2.76 g of HBr, 1.99 of Co(II) acetate tetrahydrate, and 1.99 g of Mn(II) acetate tetrahydrate. The solution was placed in a 1 liter autoclave, and heated in a nitrogen atmosphere to 400° F. (204° C.). A flow of air was then passed through the solution at a rate of approximately 0.18 SCFM at a pressure of 500 psi for 30 min. The vent dioxygen, carbon dioxide, and carbon monoxide were monitored during this period. The vent dioxygen value indicated that oxygenation was occurring. The dark solution was cooled and the mixture analyzed.

The reaction mixture was filtered through a fine glass frit and then diluted with 200 ml of ethanol to give a dark red solution. After evaporation of solvent to near the original volume, the sample was cooled to 5° C. An off-white solid, 1.8 g (7% yield) was collected, M.P. 263°–265° C. The available analytical data (one hydrogen, 13 carbons by NMR and gas chromotography-mass spectroscopy) were consistent with the bis(p-carboxyphenyl)dimethylsilane structure. Two impurities, benzoic acid and hexamethylcyclotrisilane were identified. These by-products were derived from the hydrolysis of the S-C(aryl) bond in either the feedstock or the diacid.

The mother liquor from the first crop of crystals was treated with activated charcoal and filtered through Celite. The filtrate was diluted with 200 ml of diethylether and transferred to a separatory funnel. The organic layer was washed successively with water and brine. After drying over sodium sulfate, and evaporated, repeated crystallization from ethanol/chloroform gave an additional 10.5 g (42% yield, 50% overall) of impure diacid.

EXAMPLE II

The following example illustrates that reaction temperatures in the range of from about 204° C. to about 233° C. cause decomposition of bis(p-carboxyphenyl)dimethylsilane.

Batch oxidations were conducted by charging all of the catalyst components, bis(p-tolyl)dimethylsilane and acetic acid, sealing the reactor; setting a pressure control valve to 500 psig (valve was in exhaust vent line); pressuring the reactor to 500 psig with nitrogen; heating the reactor contents to the desired temperature, 150° C. and then introducing a pressurized mixture of synthetic air (20.3% $O_2$) into the reactor at a flow rate of 0.22 SCFM. Cooling water at approximately 20° C. was introduced into the jacket of the condenser section. Temperature of the reactor was controlled via an internal cooling coil. Each oxidation was terminated when the vent gas reached a value within 1% of the synthetic air.

All oxidations were conducted initially at a gauge pressure of 500 psig, at oxidation initiation temperatures of 150° C., a weight ratio of acetic acid to bis(p-tolyl)-dimethylsilane of 20:1 and synthetic air as the source of oxygen. The oxidation reactor was a stirred 1-liter titanium cylindrical autoclave. A water-cooled condenser was placed immediately above the autoclave to condense and return a substantial portion of the volatile compounds. Following the condensation system, there were means for venting the exhaust gaseous mixture (nitrogen, unused or excess oxygen, oxides of carbon, water vapor, and vapor of uncondensed acetic acid and some of the unreacted bis(p-tolyl)dimethylsilane) and analytical means for determining the oxygen, carbon dioxide, and carbon monoxide contents of exhaust sample on acetic acid-free dry basis. The exhaust sample flowed through a "DRIERITE" trap before analysis for $O_2$, $CO_2$ and CO. The reactor was charged with 20 grams of bis(p-tolyl)dimethylsilane and 400 grams of acetic acid for a 20:1 solvent to bis(p-tolyl)dimethylsilane ratio. The temperature increased from 150°–162° C. in 33 minutes. The reactor was pressured to 500 psig with nitrogen and then heated to the initiation temperature. Thereafter pressurized synthetic air was introduced into the liquid phase in the reactor. Each oxidation was terminated when the vent oxygen reached a value within 1% of the value for the synthetic air itself, which ranged from 18 to 21% oxygen.

Reaction conditions and results given in Table I.

TABLE I

| Oxidation of Bis(p-toly)Dimethylsilane | | |
|---|---|---|
| Run No. | 11816-177 | 12635-27 |
| Reaction Conditions | | |
| Catalyst | | |
| Co(OAc)$_2$.4H$_2$O, g | 2.49 | 2.00 |
| Mn(OAc)$_2$).4H$_2$O, g | 2.48 | 2.00 |
| NaBr, g | 0.413 | 1.664 |
| HBr, (wt. % Aqueous) g | 2.76 | — |
| HOAc, g | 400 | 500 |
| Temp., °C. | 206–186 | 204–233 |
| Pres., psig | 500 | 500 |
| Time, minutes | 33 | 120 |
| Feedstock, wt. g | 19.74 | 98.69 |
| Results (yield) | | |
| Bis(p-carboxyphenyl) dimethylsilane, mole % | 50 | 0 |
| Impurities | | |
| Benzoic Acid | present | present |
| Hexamethylcyclo- trisilane | present | present |
| Others | present | present |

EXAMPLE III

The following example illustrates that a reaction temperature of less than about 100° C. results in an unsatisfactory yield of product in oxidation of bis(p-tolyl)-dimethylsilane to bis(p-carboxyphenyl)dimethylsilane.

In the procedure of Example II, bis(p-tolyl)dimethylsilane was oxidized under the conditions given in Table II.

TABLE II

| Run No. | No. 82 |
|---|---|
| Reaction Conditions | |
| Catalyst | |
| Co(OAc)$_2$.4H$_2$O, g | 1.50 |

TABLE II-continued

| Run No. | No. 82 |
| --- | --- |
| Mn(OAc)$_2$.4H$_2$O, g | 1.49 |
| NaBr, g | 1.73 |
| Solvent | 400 |
| Acetic acid, g | |
| Temp., °C. | 93–107 |
| Pres., psig | 500 |
| Time, minutes | 58 |
| Feedstock, wt. g | 19.94 |

Product yield was 45 mole %, as determined by gas chromatographic (GC) method. Impurities were benzoic acid, hexamethylcyclotrisiloxane, and (p-carboxy p-tolyl) dimethylsilane.

EXAMPLE IV

The procedure of Example III was repeated with all reaction conditions identical with reaction conditions of Example III, except that reaction temperature was within the range of 121° C. to 131° C., and reaction time was 50 minutes. Product yield was 82 mole % by GC method. Impurities were benzoic acid and hexamethylcyclotrisiloxane.

EXAMPLE V

The procedure of Example III was repeated with all reaction conditions identical with reaction conditions of Example III except that reaction temperature was 149° C. to 163° C., 5 wt. % water was added to the glacial acetic acid, and reaction time was 43 minutes. Product yield was 84 mole % by GC method. Impurities were benzoic acid and hexamethylcyclotrisiloxane.

EXAMPLE VI

The following example illustrates that an increased weight of feedstock to the aliphatic C$_2$ to C$_6$ monocarboxylic acid increases product yield.

The procedure of Example V was repeated but with an added amount of feedstock, 40.00 g versus 19.95 g as in Example V. Weight ratio of feedstock to acetic acid was about 1:10. Product yield after reaction time of 70 minutes was 90 mole % by GC method. Impurities were benzoic acid and hexamethylcyclotrisiloxane.

EXAMPLE VII

The procedure of Example IV was repeated with all reaction conditions identical with reaction conditions of Example III except that reaction temperature was within the range of from 150° C. to 162° and run time was 33 minutes. Product yield was 92 mole % by GC method. Impurities were benzoic acid and hexamethylcyclotrisiloxane.

EXAMPLE VIII

The procedure of Example VII was repeated with all reaction conditions identical with the reaction conditions of Example VII except that the feedstock was bis(3,4-dimethylphenyl)dimethylsilane. Reaction temperature was with the range of from 143° C. to 161° C. and run time was 38 minutes. Product yield was undetermined. Impurities identified were phthalic anhydride, phthalic acid and hexamethylcyclotrisiloxane.

EXAMPLE IX

The following illustrates a continuous procedure for oxidation of bis(p-tolyl)dimethylsilane to bis(p-carboxyphenyl)dimethylsilane.

Into a suitable reactor, maintained at a pressure within the range of from about 300 psig to about 600 psig, there is introduced a feedstock comprising bis(p-tolyl)dimethylsilane, a solvent comprising glacial acetic acid, a catalyst comprising cobalt-manganese-bromine wherein the weight ratio of cobalt, calculated as elemental cobalt, in the cobalt component of the catalyst to the bis(p-tolyl)dimethylsilane is about 60 milligram atoms (mga) per gram mole of bis(p-tolyl)dimethylsilane, wherein mole ratio of manganese to cobalt is about one mga per one mga of cobalt and the bromine component (calculated as elemental bromine) is about one mga per one mga of total cobalt and manganese, and glacial acetic acid, wherein said feedstock and said glacial acetic are present in a weight ratio of about 1:5, feedstock to acetic acid, and wherein water content of the reaction mixture is less than 0.5 wt. %.

Reaction temperature is maintained at a temperature within the range of from 150° C. to 165° C. Reaction pressure is about 300 psig. Oxygen concentration (measured on a solvent-free basis) in the vent gas-vapor mixture is less than 8 vol. %, maintained by the feed rate. Residence time is about 1 hour.

From the exit end of the reaction zone, there is withdrawn an effluent comprising bis(p-carboxyphenyl)-dimethylsilane, by-product oxygenated compounds, inert gases and unreacted feedstock and oxygen. The effluent is passed to a separation zone wherein product and by-products are recovered. The remaining effluent is dehydrated and recycled to the reaction zone.

What is claimed is:

1. A process for preparation of silicon-containing aromatic polyacids by liquid phase oxidation of an alkyl-substituted diaryldialkylsilane wherein alkyl groups containing 1 to 20 carbon atoms in the alkyl-substituted diaryl group number from 1 to 4, and the number of carbon atoms is from 1 to 20 in the alkyl groups attached to the silicon of the silane group, which process comprises:
   (a) introducing into a suitable reactor a feedstock comprising said alkyl-substituted diaryldialkylsilane in a solvent acid comprising an aliphatic C$_2$ to C$_6$ monocarboxylic acid;
   (b) oxidizing said feedstock in the presence of a catalyst comprising cobalt-manganese-bromine with an oxygen-containing gas wherein the weight ratio of cobalt (calculated as elemental cobalt) to the alkyl-substituted diaryldialkylsilane is in the range of from about 0.2 to about 100 milligram atoms (mga) per gram mole of said alkyl-substituted diaryldialkylsilane, weight ratio of manganese (calculated as elemental manganese) to the cobalt of said catalyst is in the range of from about 0.2 to 100 milligram atoms (mga) per mga of cobalt, and weight ratio of bromine in said catalyst (calculated as elemental bromine) to total cobalt and manganese (calculated as elemental cobalt and manganese) is in the range of from about 0.25 to about 1.2 mga per mga of total cobalt and manganese, wherein weight ratio of said feedstock to said aliphatic C$_2$ to C$_6$ monocarboxylic acid is from about 1:5 to about 1:10, said feedstock to said acid, at a temperature within the range of from about 120° C. (250° F.) to about 260° C. (500° F.) and at a reaction pressure within the range of from about 50 psig to about 750 psig; and
   (c) recovering a silicon-containing aromatic polyacid wherein said polyacid comprises a bis(mono- or polycarboxyaryl)dialkylsilane.

2. The process of claim 1 wherein said feedstock comprising an alkyl-substituted diaryldialkylsilane is selected from the group consisting of bis(p-tolyl)dimethylsilane and bis(3,4-dimethylphenyl)-dimethylsilane.

3. The process of claim 1 wherein said feedstock comprises bis(p-tolyl) dimethylsilane, said $C_2$ to $C_6$ monocarboxylic acid is acetic acid, and said silicon-containing aromatic polyacid comprises bis(p-carboxyphenyl) dimethylsilane.

4. The process of claim 1 wherein said feedstock comprises bis(3,4-dimethylphenyl)dimethylsilane, said $C_2$ to $C_6$ monocarboxylic acid is acetic acid, and said silicon-containing aromatic polyacid comprises bis(3,4-dicarboxyphenyl)dimethylsilane.

5. The process of claim 1 wherein said oxygen-containing gas is air.

6. The process of claim 1 wherein said process is a continuous process wherein the feedstock is selected from the group consisting of bis(p-tolyl)dimethylsilane and bis(3,4-dimethylphenyl)dimethylsilane, the $C_2$ to $C_6$ monocarboxylic acid is acetic acid, the mole ratio of manganese to cobalt is in the range of from about 0.2 to about 10.0, mole ratio of bromine to total cobalt plus manganese is about 0.2 to about 1.2, weight ratio of cobalt to said acetic acid, as glacial acetic acid, is in the range of from about 250 ppm to about 750 ppm, water content of the reaction mixture is from about 0.5 wt. % to about 2.0 wt. % reaction temperature is in the range of from about 140° C. to about 165° C., reaction pressure is within the range of from about 200 psig to about 550 psig, wherein said oxygen-containing gas fed to said reactor provides an exhaust gas-vapor mixture containing from 0.5 to 8 volume percent oxygen, measured on a solvent-free basis and residence time is from about 30 minutes to about 6 hours.

* * * * *

UNITED STATES PATENT OFFICE
CERTIFICATE OF CORRECTION

Patent No. 4,940,810                    Dated July 10, 1990

Inventor(s) Howard B. Yokelson, Walter Partenheimer, Robert Gipe

It is certified that error appears in the above-identified patent and that said Letters Patent is hereby corrected as shown below:

| Col. | Line | |
|---|---|---|
| 1 | 43 | "ditolydimethylsilane" should be --ditolyl-dimethylsilane-- |
| 1 | 49 | "reacted.with" should read --reacted with-- |
| 1 | 57 | "ditolydiphenylsilane" should read --ditolyldiphenylsilane-- |

Signed and Sealed this

Seventeenth Day of September, 1991

Attest:

HARRY F. MANBECK, JR.

*Attesting Officer*     *Commissioner of Patents and Trademarks*